US009286440B1

(12) United States Patent
Carter et al.

(10) Patent No.: US 9,286,440 B1
(45) Date of Patent: Mar. 15, 2016

(54) SELF-CONTAINED EMERGENCY SITUATION ASSISTANCE KIT WITH PROGRAMMED AUDIO AND VISUAL INSTRUCTIONS

(75) Inventors: Annette Carter, Cedar Rapids, IA (US); Paula Wickham, Cedar Rapids, IA (US); Kirk Dighton, Walker, IA (US); Troy Mundt, North Liberty, IA (US)

(73) Assignee: RETRAC, INC., Cedar Rapids, IA (US)

( * ) Notice: Subject to any disclaimer, the term of this patent is extended or adjusted under 35 U.S.C. 154(b) by 1851 days.

(21) Appl. No.: 11/759,618

(22) Filed: Jun. 7, 2007

Related U.S. Application Data

(63) Continuation-in-part of application No. 11/160,245, filed on Jun. 15, 2005, now Pat. No. 8,647,123.

(60) Provisional application No. 60/804,373, filed on Sep. 9, 2006.

(51) Int. Cl.
*G06F 15/00* (2006.01)
*G06F 19/00* (2011.01)

(52) U.S. Cl.
CPC .................. *G06F 19/3406* (2013.01)

(58) Field of Classification Search
USPC .............................. 434/262; 206/570; 607/5
See application file for complete search history.

(56) References Cited

U.S. PATENT DOCUMENTS

| 4,290,114 A * | 9/1981 | Sinay ........................... 600/301 |
| 4,303,395 A | 12/1981 | Bower |
| 4,513,866 A | 4/1985 | Thomas |
| 4,839,822 A * | 6/1989 | Dormond et al. ............... 706/45 |
| 5,086,391 A | 2/1992 | Chambers |
| 5,088,037 A * | 2/1992 | Battaglia ...................... 600/300 |
| 5,515,974 A * | 5/1996 | Higson ......................... 206/570 |
| 5,521,812 A | 5/1996 | Feder et al. |
| 5,576,952 A * | 11/1996 | Stutman et al. ............... 600/300 |
| 5,581,730 A * | 12/1996 | Silla ............................. 711/144 |
| 5,644,294 A * | 7/1997 | Ness ............................ 340/540 |
| 5,668,954 A | 9/1997 | Feder et al. |
| 5,848,700 A | 12/1998 | Horn |
| 5,850,630 A | 12/1998 | Wilson |
| 5,868,669 A * | 2/1999 | Iliff .............................. 600/300 |
| 5,931,304 A * | 8/1999 | Hammond .................... 206/570 |
| 6,024,699 A * | 2/2000 | Surwit et al. ................. 600/300 |
| 6,117,073 A * | 9/2000 | Jones et al. ................... 600/300 |

(Continued)

*Primary Examiner* — Timothy Musselman
*Assistant Examiner* — Alvin Carlos
(74) *Attorney, Agent, or Firm* — Zarley Law Firm, P.L.C.

(57) ABSTRACT

An emergency response information and supply system, software and method capable of providing audio and/or visual or video instructions as to how to use the medical supplies contained in the kit and location information to emergency professionals. The system is organized so that the medical supplies for different traumas or emergency situations are packaged into individual and separated bags. The user can activate the audio and/or visual or video instructions by pushing at least one button on the unit's console that corresponds to the particular trauma or emergency event. Alternatively, instructions can be activated by removing a bag from the case which automatically begins the instructions. If a victim has sustained multiple injuries and the user has depressed multiple buttons or removed multiple bags, then the device automatically prioritizes the emergency situations and provides instructions on the appropriate emergency response to provide and in the proper order. The system can potentially notify emergency professionals and provide information on the status of a patient or first responder using the system.

20 Claims, 7 Drawing Sheets

(56) References Cited

U.S. PATENT DOCUMENTS

| | | | |
|---|---|---|---|
| 6,286,682 B1 * | 9/2001 | d'Arbelles | 206/570 |
| 6,321,113 B1 * | 11/2001 | Parker et al. | 607/5 |
| 6,346,886 B1 * | 2/2002 | De La Huerga | 340/573.1 |
| 6,383,135 B1 * | 5/2002 | Chikovani et al. | 600/300 |
| 6,454,097 B1 * | 9/2002 | Blanco | 206/570 |
| 6,460,702 B2 | 10/2002 | Hammond | |
| 6,468,210 B1 * | 10/2002 | Iliff | 600/300 |
| 6,475,143 B2 * | 11/2002 | Iliff | 600/300 |
| 6,771,172 B1 * | 8/2004 | Robinson et al. | 340/573.1 |
| 6,957,738 B2 * | 10/2005 | Hammond | 206/570 |
| 7,149,693 B2 * | 12/2006 | Laronne et al. | 704/270 |
| 7,259,667 B2 * | 8/2007 | Sergio et al. | 340/539.11 |
| 2002/0004729 A1 * | 1/2002 | Zak et al. | 705/3 |
| 2002/0078966 A1 * | 6/2002 | Lewis | 128/897 |
| 2002/0104774 A1 * | 8/2002 | Hammond | 206/570 |
| 2002/0120187 A1 * | 8/2002 | Eiffert et al. | 600/407 |
| 2002/0178275 A1 * | 11/2002 | Hein et al. | 709/231 |
| 2003/0023461 A1 * | 1/2003 | Quintanilla et al. | 705/3 |
| 2003/0146942 A1 * | 8/2003 | Helgason et al. | 345/968 |
| 2003/0208357 A1 | 11/2003 | Hammond | |
| 2004/0038190 A1 * | 2/2004 | Abraham-Fuchs et al. | 434/262 |
| 2004/0064342 A1 * | 4/2004 | Browne et al. | 705/2 |
| 2004/0084047 A1 * | 5/2004 | Hickle | 128/203.13 |
| 2005/0015115 A1 | 1/2005 | Sullivan et al. | |
| 2005/0177393 A1 * | 8/2005 | Sacco et al. | 705/2 |
| 2006/0111749 A1 * | 5/2006 | Westenskow et al. | 607/5 |
| 2006/0111933 A1 * | 5/2006 | Wheeler | 705/2 |
| 2006/0197656 A1 * | 9/2006 | Sergio et al. | 340/539.11 |

* cited by examiner

SELF-CONTAINED EMERGENCY SITUATION ASSISTANCE KIT WITH PROGRAMMED AUDIO AND VISUAL INSTRUCTIONS

CROSS-REFERENCE TO RELATED APPLICATIONS

This is a continuation-in-part application of an application filed by the same inventors herein on Jun. 15, 2005, having application Ser. No. 11/160,245, entitled "FIRST RESPONDER EMERGENCY SITUATION ASSISTANCE DEVICE". This current application also claims the benefit of a provisional application filed by the same inventors herein on Jun. 9, 2006, Application No. 60/804,373, entitled "SELF CONTAINED EMERGENCY SITUATION ASSISTANCE KIT WITH PROGRAMMED AUDIO AND VISUAL INSTRUCTIONS".

BACKGROUND OF THE INVENTION

In the United States, there were over 27,000,000 nonfatal injuries reported as being treated by hospital emergency departments in 2002. The National Safety Council statistics showed 20,400,000 unintentional disability injuries and 99,500 unintentional deaths in the U.S. for that same year. For each of these traumas, there is a period of time known as a "gap." The gap is that period of time where family, coworkers, or other bystanders with little or no medical training are at the scene of an accident attempting to assist the victim. A national standard shows the average urban response time (the gap) for advanced care is 8.5 minutes. Rural response times have not been established, but they are suspected to be somewhat longer than the average urban response time.

The gap is the most important time period in which to prevent further damage to the victim and help to preserve a victim's life. Victims who receive definitive, necessary and proper care in airway management, choking, bleeding, and management of burns within the first five minutes of injury are more likely to have minimal damage. In some cases, incorrect assistance can cause more damage to the victim than no assistance at all. Thus, an individual at the scene of an accident with limited knowledge and resources makes crucial decisions that can positively or negatively affect human life.

The American Red Cross has identified that even people who have taken first-aid classes may not remember what to do in an emergency situation. Their studies have shown that the retention rate of the skills covered in a first-aid class decreases after six weeks and is likely gone after six months. This lack of retention is magnified when the stress and panic of an actual trauma is presented. It is, therefore, crucial that the person administering the assistance stay calm so as to better remember what steps to take to help the victim.

Traditional first responder kits are inefficient for several reasons. First, traditional kits provide supplies with only written instructions on their usage. This can either increase the time it takes for the person to provide assistance to the victim, or it can lead to incorrect assistance if the person decides not to read the instructions before administering assistance. Second, traditional kits do not organize supplies by type of trauma; rather, they package supplies together with like supplies. For example, rubber gloves and band-aids are packaged together with various sized gloves and assorted band-aids even though the entire box will not be used during one trauma. This packaging system can add to confusion for the person administering the first aid because the person may not remember what supplies or medications should be used to treat the trauma. Finally, traditional kits do not assist in helping to calm the person administering the aid or provide immediate prompting as to how to address the trauma situation or multiple situations. This can lead to incorrect actions by the person administering the first aid, or it may decrease the chances that a bystander will remember what to do for the trauma situation.

There are several known devices which are directed toward first-aid kits. These devices include U.S. patent application Ser. No. 10/140,462 and U.S. Pat. Nos. 5,850,630 and 6,460,702. Some of these devices disclose a means for providing audio instructions to the caregiver which help the caregiver remember how to provide assistance to victims in certain trauma situations. The problem with these devices is that they do not offer the ability to prioritize which trauma is most important when the victim has sustained multiple traumas. In other words, an inexperienced caregiver may tell the device to give instructions for bleeding when proper medical procedure would actually call for the caregiver to be doing CPR on the victim first. Further, the devices disclosed in these patents are inefficient because they require the user to turn them on and then correctly select the instructions for the appropriate trauma. In the stress of an emergency situation, it is likely that the user will make a mistake and incorrectly press buttons on the console, which can cause more harm to the victim because more time passes before the first aid is administered.

Therefore, there is a need for a medical supply kit that is able to help laypersons calmly and efficiently provide assistance to a victim or several victims in an emergency situation and prioritizes the severity of the victims' traumas in a multiple trauma situation.

SUMMARY OF THE INVENTION

The present invention is an emergency response information and supply system, software, and method adapted to provide audio and/or video instructions to the user as to how to use the supplies contained in the kit, as well as potentially location information to emergency responders, or emergency medical and rescue professionals. The kit comprises a case which contains a plurality of bags carried by the case. Each bag contains medical supplies aimed at addressing one particular type of trauma situation. Each bag is comprised of a unique color and number allowing for quick reference, as is further described below. A brief description of the trauma that the supplies in the bag are aimed at addressing is printed on the outside of the bag.

The kit further comprises a console having a plurality of buttons and other types of switches for controlling the audio and/or video instructions. The color, number, and printed trauma description on each bag corresponds to the color, number, and trauma description associated with one of the buttons on the unit's console. As indicated above, the programmed instructions can be audio, visual, or both. Pressing one of the buttons begins the instructions for treating the trauma indicated by that button or by directing them to the appropriate emergency protocols within a different button, if there is a more urgent priority for the responder to address. If the user pushes multiple buttons or the multiple injury button signifying that the victim has sustained multiple traumas, the device prioritizes the traumas by asking specific interactive yes/no questions that tie to algorithms on correct standard medical procedures and protocols to follow. Additionally, all buttons have embedded questions that tie to other traumas and take the responder to the appropriate emergency procedures to address and in the right order. For example, if the bleeding button is pressed it will ask, "Is the victim conscious and breathing?" one of several key questions that if answered NO, then it takes responders to CPR button protocols. If YES is answered, then it proceeds with questions that will prioritize treatment of bleeding situations. The buttons on the console allow the user to skip forward, pause, rewind, and otherwise efficiently navigate the audio and/or video instructions in the event of a mistakenly pressed button or other reason for navigation.

In addition to, or as an alternative to pressing a button to begin the instructions, the audio and/or video instructions can be activated by simply opening or removing a bag from the case. In this embodiment, the bags are connected to the case in such a manner that removing a bag from the case automatically begins the audio and/or video instructions for the trauma associated with the removed bag(s). This reduces the amount of time the user spends determining which button(s) to push and allows the user to immediately obtain the necessary supplies contained in the removed supply bag. If multiple bags are removed, thereby signifying that the victim has sustained multiple traumas, the device prioritizes the traumas and gives instructions in the order that the traumas should properly be addressed according to standard medical procedures and protocols, regardless of the order in which bags were removed.

In addition to audio and/or video instructions, the case includes a first-aid or emergency response instruction booklet and an overview card for each bag. It should be noted that the printed instructions will typically not be used in an emergency situation unless the audio/video instruction system fails. The overview card is color coded and numbered so as to correspond with the appropriate bag and console button. The instruction booklet has tabs that are color coded and numbered so as to correspond with the bags, buttons, and overview cards. The instruction booklet and/or overview cards have instructions and illustrations on how to address trauma situations, such as diagrams that show where to apply CPR compressions on a person's chest.

The audio and/or video instructions guide inexperienced persons or out-of-practice first responders through the treatment of any trauma, including a multiple injury trauma so as to address the situation in a calm and proper manner. The benefit of the invention is that the device allows for prompt audible instructions that address a situation or addresses and prioritizes multiple situations. The user can listen to the instructions without having to take time to read anything and pull out a reference manual so as to more quickly assess an urgent situation and address it. An additional advantage is that the case can be easily re-stocked by simply re-stocking the particular bag(s) that was needed to address the trauma. This increases efficiency and decreases waste by allowing the user to re-stock only the medical supplies that have been used instead of having to purchase an entirely new first-aid kit to replace only a few medical items. The device allows for readily accessible instructions for emergency protocols that would apply to any major emergency situation that surfaces quickly, even if in the middle of a different emergency, allowing for proper priority to be taken into consideration.

This device provides confidence and comfort for businesses, families, and individuals who may be confronted with an unexpected emergency. The device provides the victim with immediate and efficient care during the gap period and thus provides a better chance of survival and less chance of disability for the victim.

DESCRIPTION OF THE PREFERRED
EMBODIMENT OF THE INVENTION

The present invention is a self-contained emergency supply kit capable of providing audio and/or video instructions to the user as to how to use the medical supplies contained in the kit. It should be noted that although the majority of this specification describes the invention as a first-aid or emergency response tool, the kit can be used for any suitable application, including as a pediatric or advanced medical assistance kit, HAZMAT or CBRNE event preparedness, wilderness or adventure survival kit, disaster preparedness kit, or natural disaster (i.e., earthquake, hurricane) survival kit. Examples of the types of traumas that the kit may address include CPR, choking, allergic reactions, bites & stings, bleeding, head/spine injuries, eye injuries, cardiac events, seizures, radiation poisoning, fractures/sprains, burns, poisoning, and heat stress/overexertion. Of note is that the system when used for first aid or basic life support is designed using reference material from American Red Cross, American Heart Association, Medic First Aid and other top safety and first aid training organizations.

Figure 1:
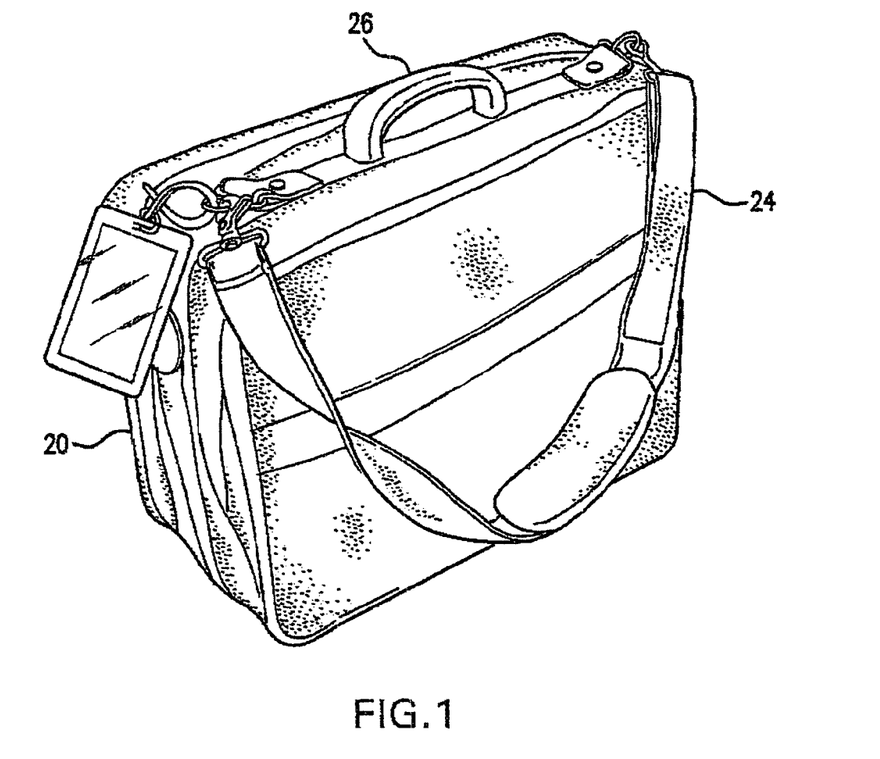
FIG. 1 is a perspective view of the present invention showing the case in the closed position.
Figure 2:
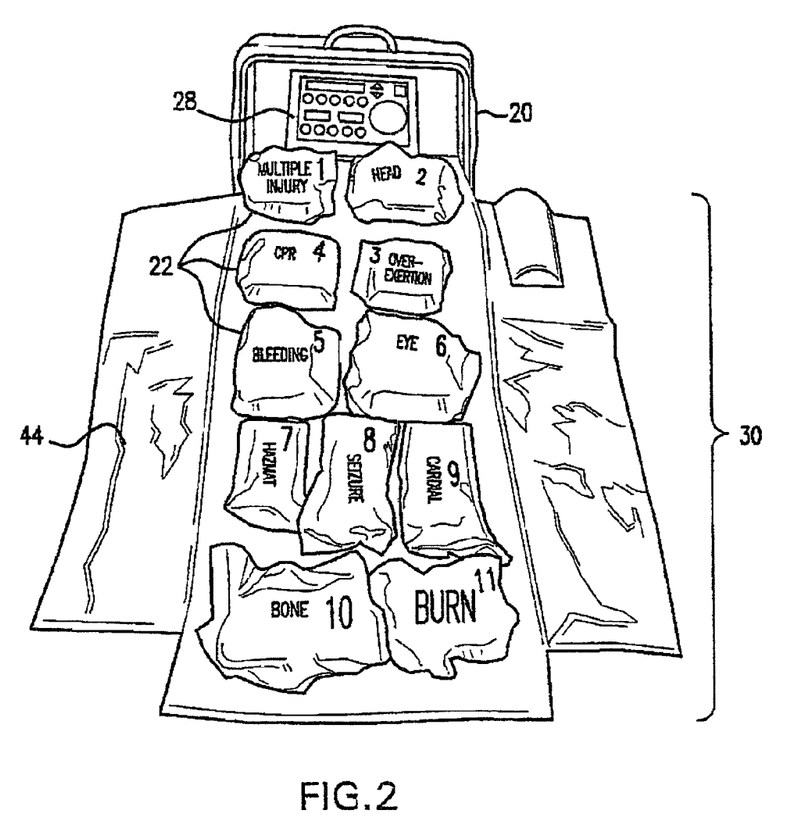
FIG. 2 is a perspective view of the present invention showing the case in the open position and the break-away bags containing the supplies.

As shown in FIGS. 1 and 2, the kit comprises a case 20 having a plurality of bags 22 containing supplies. The bags 22 are attached to the case 20 in a roll-out fashion, as is further described below. The case 20 can be opened and closed using a zipper or any other suitable means so as to protect the contents of the case 20 when the case 20 is closed and not in use. The case 20 preferably has a handle 26 and a shoulder strap 24 to aid in carrying it. Additional medical supplies not contained in the individual bags 22 may be contained in the top, bottom, or sides of the case 20. Preferably, the case 20 has an inspection tag adapted to allow users to declare and sign off as to when the kit was last inspected and stocked.

Each of the plurality of bags 22 contain supplies adapted for treating one particular kind of emergency situation. Each bag 22 is a different color and may be numbered with a different number printed on each bag to allow for quick reference. A brief description of the trauma that the supplies in each bag 22 address is printed on the outside of the bags 22. Preferably, as shown in FIG. 2, the bags 22 are combined with a portion of the case 20 referred to as the roll-out portion 30. The roll-out portion 30 rolls up for storage in the case 20 when the case 20 is in the closed position, and quickly rolls out to display the bags 22 when the case 20 is in the open position. In its extended position, the roll-out portion 30 allows the user to quickly see all of the bags 22 contained in the case 20 without having to open additional pouches or dig through other supplies that may be contained in the case 20. The bags 22 are combined with the roll-out portion 30 in such a manner that they can easily be detached from the roll-out portion 30.

As seen in FIG. 2, the roll-out portion 30 preferably has flaps 44 to help contain and protect the bags 22 when the device is not in use. The roll-out portion 30 of the case 20 is preferably detachable from the case 20 for cleaning purposes and preferably made of a fabric such as nylon, so that it is durable, yet flexible.

Figure 3:
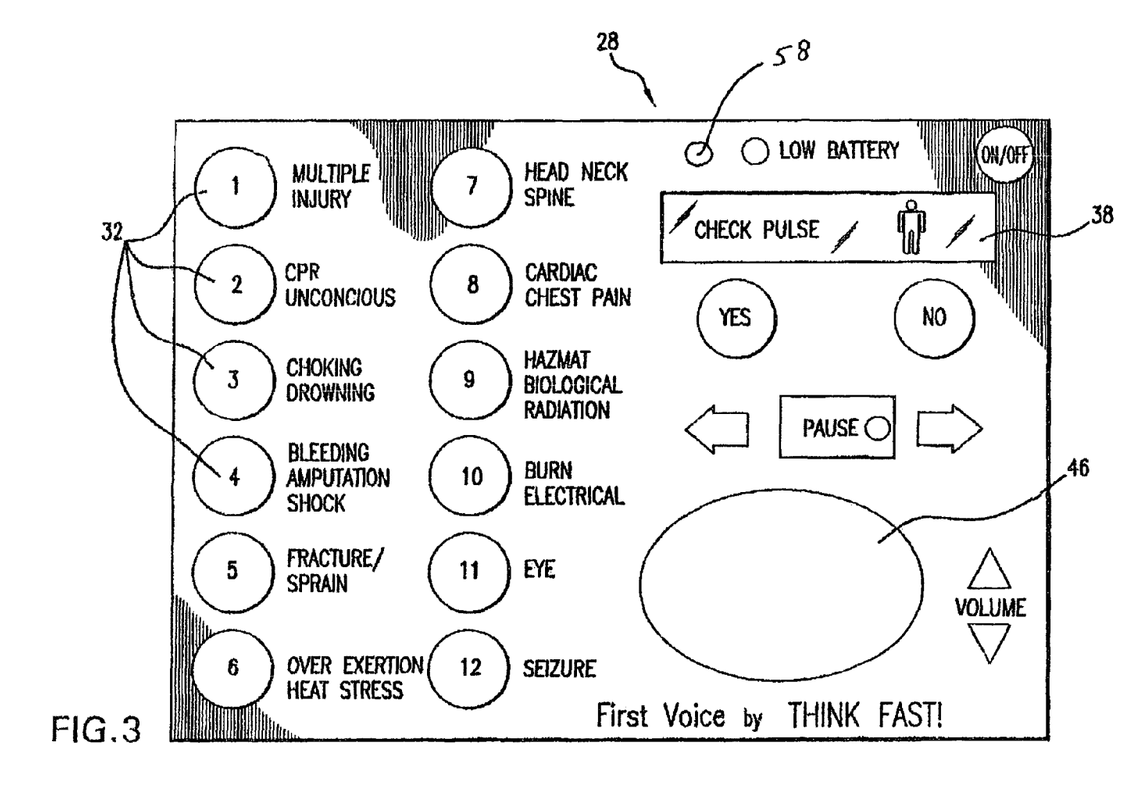
FIG. 3 is a perspective view of the case's console.

As shown in FIGS. 2 and 3, the kit further comprises a console 28. In the preferred embodiment, the console 28 is removable from the case 20, so that the user can easily position it in a convenient location when receiving and navigating the instructions and administering assistance to the victim. The console 28 has a plurality of switches for controlling the circuitry related to the audio and/or video instructions. The switches can be buttons, levers, knobs, or any other suitable means for providing signals to the circuitry of the device. The console 28 could be a multi-purpose device, such as a PDA or tablet PC with a touch-screen capability. In such cases, the switches could be "soft switches" which are configurable positions on the screen which act as buttons when touched, etc. The switches may control functions such as volume, pause, rewind, restart, power, skip ahead, language selection, and any other suitable function that allows the user to efficiently navigate the audio and/or video instructions. Some of the switches have a color, number, and trauma description associated with them that correspond with a bag 22 having the same color, number, and description. These switches are called task selection keys 32, which are further described below. In the preferred embodiment, the console 28 also comprises "yes" and "no" switches which aid the user in the navigation of the audio and/or video instructions. For example, the audio instructions may ask the user if the bleeding has stopped, to which the user would press either the "yes" or "no" switch, which would prompt the device as to which set of pre-recorded instructions to provide to the user. In an alternate embodiment, the kit may comprise voice recognition software that allows the device to respond to verbal commands given by the user. This embodiment would improve the speed and efficiency with which a user could provide first-aid treatment to a victim because the user would not have to spend time pressing the various switches; instead, the user would only have to verbally speak the commands to the device.

Figure 6:
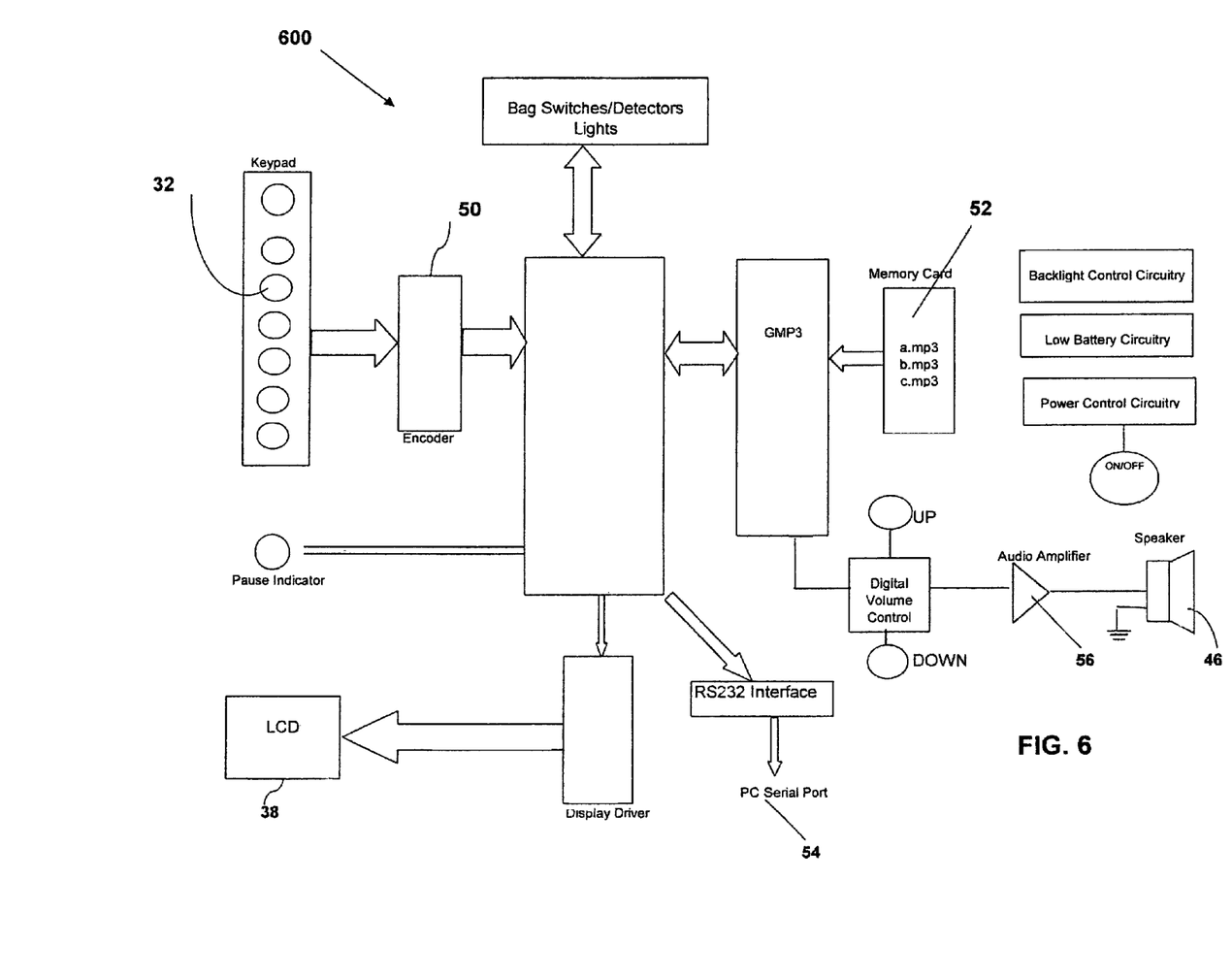
FIG. 6 is a diagram of the circuitry for the electronic automated voice unit.

FIG. 6 shows a schematic of the circuitry of the kit. Among other things, FIG. 6 shows that the invention comprises a voice unit which has a means for providing audible instructions to the user. The voice unit includes a speaker 46 mounted in the console 28 for projecting the audible instructions and a memory for storing the instructions in electronic format. The audible instructions can be activated by one of several ways. First, the instructions can be activated by pushing one or more of the plurality of color-coded and numbered task selection keys 32 on the console 28. All color-coded and numbered task selection keys 32 correlate to the colored and numbered bags 22 attached to the case 20. The bag 22 that corresponds to the task selection key 32 contains medical supplies aimed at treating the indicated trauma. As seen in FIGS. 2 and 3, both the keys 32 and the bag 22 have a description of the trauma printed on them.

Figure 4:
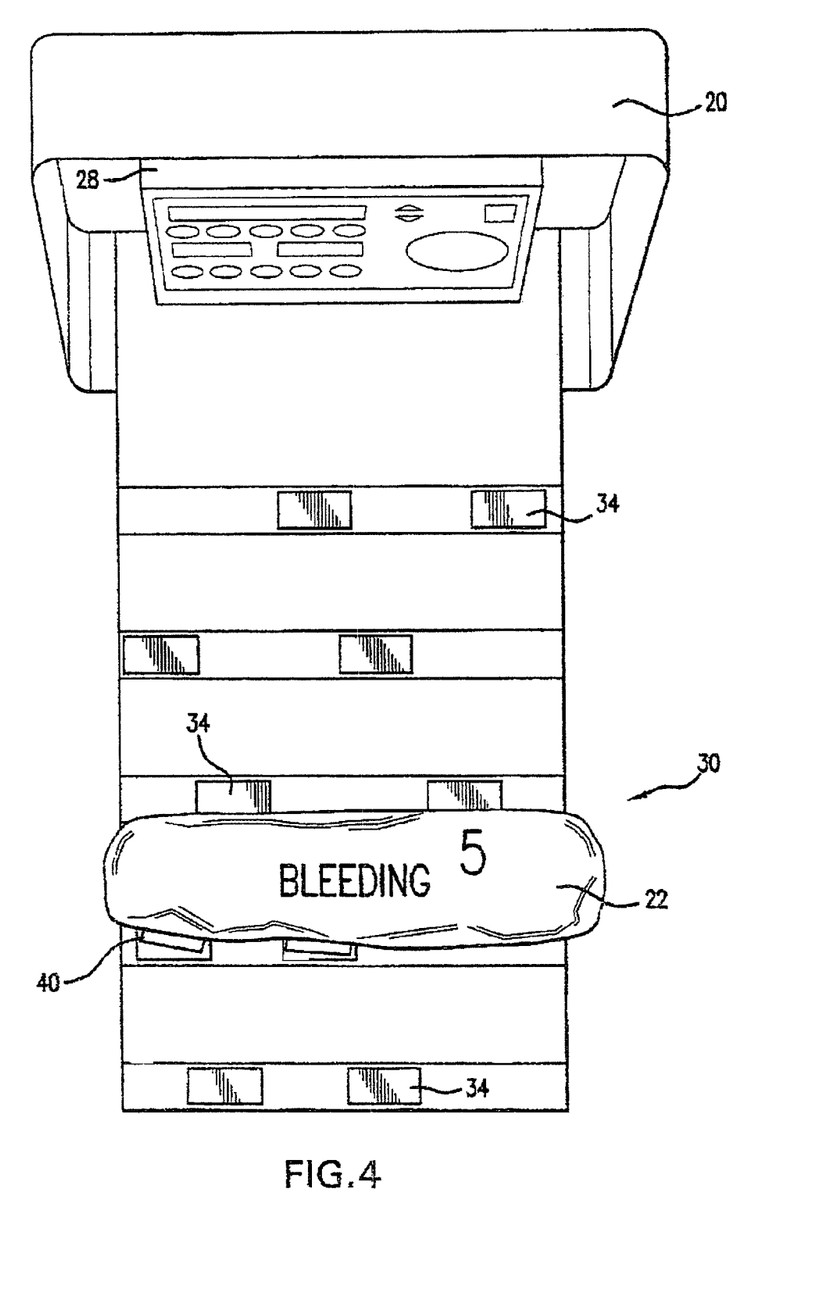
FIG. 4 is a top view showing the connection points on the roll-out portion of the case which combine with the break-away bags.

In an alternate embodiment shown in FIG. 4, the bags 22 are combined with the roll-out portion 30 of the case 20 by a connector. In the preferred embodiment, the connector is an electronic switch 34 means which triggers the audio/video instructions when a bag 22 is removed from the case 20. The term for the bags 22 in this embodiment is "break-away" bags 22, since breaking them away from the case 20 automatically triggers the start of the instructions.

In this embodiment, the switch 34 used to trigger the break-away bags 22 is a magnetic switch 34; other arrangements could be used, such as RFID tag and readers. In such RFID arrangements, the bag could be constructed that once the bag is pulled from the roll out portion of the bag, the RFID tag is enabled or disabled and detected by a tag reader. In the alternate embodiment where the magnet(s) 40 is combined with the bag 22, a magnetic switch 34 is combined with the roll-out portion 30 of the case 20. When the magnet 40 on the bag 22 is no longer in close proximity to the switch 34, an electronic signal tells the device that the bag 22 has been removed. The device then begins the instruction sequence for the trauma associated with the removed bag 22. As seen in FIG. 4, the positioning of the switches 34 and corresponding magnets 40 on each bag 22 is unique, so that each bag 22 can only be combined with the roll-out portion 30 in one location. This prevents bags 22 from being attached to the wrong location on the roll-out portion 30 which could result in the wrong instructions being given for a particular bag 22. When the bags 22 are all combined with the roll-out portion 30, or when power is first applied, the device will automatically check to determine whether all bags 22 are in their proper location on the roll-out portion 30. The device will indicate to the user whether the bags 22 are correct, or whether a bag 22 is incorrect or missing.

As discussed above, pressing one of the keys 32 or removing one of the break-away bags 22 begins the instructions for treating the indicated trauma. If the user pushes multiple keys 32 or removes multiple bags 22, thereby signifying that the victim has sustained multiple traumas or injuries (or signifying multiple emergency situations are present), the device will prioritize the traumas/situations and give instructions in the order that they should properly be addressed according to standard procedures or protocols for emergency/pre-hospital medical care, regardless of the order in which the user pressed the keys 32 or removed the bags 22. Once the pertinent bags 22 have been pulled from the unit (or keys 32 have been pushed), indicating a multiple injury or multiple emergency response situation, the priority rules which have been established by standard medical procedures and programmed into the circuitry of the device give instructions on the most urgent situation first. In instances where it is hard to assess which injury is more urgent, the device will prompt the user as to which trauma to address first, using a series of stored "yes" or "no" questions to which the user will respond using the "yes" and "no" buttons on the console 28. The device contains software adapted to prioritize instructions obtained from a programmed predetermined set of rules based on bag 22/selection key 32 input, as well as the "yes"/"no" input provided by the user.

The electronic automated voice unit is the preferred means for communicating instructions to the user as discussed above; however, there are several other means for communicating instructions to the user. As shown in FIG. 3, the instructions may be presented in video format, either using pictures or printed language on a video display screen 38. In this video embodiment, the console 28 of the device preferably has a liquid crystal display (LCD) or video display 38 that, among other things, reminds the user to continually assess the vital signs of the victim as a means of trying to decrease victim fatality or disability due to addressing one emergency situation but forgetting to re-assess vital signs (breathing, pulse, etc.) while completely addressing the one situation. The video display 38 can also provide abbreviated visual instructions using words or pictures. For example, the video screen 38 may show a diagram of a human body with arrows pointing to the proper location of applying chest compressions when administering CPR. The video instructions may be activated and navigated in the same manner as the audio instructions discussed above.

The audio and/or video components of the present invention are powered by a power supply contained in the case. In the preferred embodiment, the power supply is a battery pack that may be rechargeable. The audio instructions are preferably stored on an embedded MP3 player to play voice files which are stored under an MP3 format or other audio sound file format. This is shown in FIG. 6, which shows the preferred circuitry for the device. The MP3 format files or other form of audio files will be played via the assistance of a microcontroller and an encoder 50. The unit will preferably employ a removable flash memory card 52 to store voice files or other means for storing memory and allow for ease of file updates using a USB port or other port 54. The microcontroller will receive inputs on which voice file or software code/script to play or what action to take from the console 28/keypad buttons 32 on the device or via the switches 34 from roll-out portion 30 of the bag 20. Once the microcontroller identifies from the keypad or switches 34 the proper voice files or software code to play, it is played via the assistance of an audio amplifier 56 and outputs to a speaker 46. The speaker 46 volume is controlled via volume keys on the console 28 of the device. The microcontroller also drives the video display 38. Proper visual instructions are played on the video display 38 with the assistance of the display driver. The visual instructions are displayed after the microcontroller identifies from the console 28 or the switches 34 which instructions or coding is to be played/shown in conjunction with the proper voice instruction from the speaker 46 output.

In the preferred embodiment, the device has several features that add to the efficiency and reliability of the device. First, the device preferably is adapted to receive an ear plug or headphone jack that allows the user to hear the audio instructions more easily in a loud environment, such as a factory or road-side application. Second, the device preferably has a low battery indicator light which will flash and prompt a loud beeping sound from the case to indicate that the batteries need to be replaced. Third, the device preferably has an auto shut-off feature that turns the device off if the unit has not been used after a predetermined amount of time. Fourth, the device preferably has a global positioning system (GPS) receiver enclosed which enables emergency services to pinpoint the location of the device and more easily be directed to the victim. The GPS receiver can be activated either automatically, or when the user pushes a designated button 58 on the console 28. Fifth, the device may include a transmitter which is adapted to call emergency services, such as 911, either automatically or when the user pushes a designated button on the console 28. Finally, the device preferably has the capability to allow for a USB port or other port to allow for downloading new or updated information or software upgrade into the unit in the future. FIG. 6 shows a PC serial port which allows for updated information or updated/amended software code to be stored on the microcontroller for future use by the electronic unit.

The case 20 also may include several "upgradeable" supplies stored in various portions of the case 20. These supplies can help an experienced first responder from a specific market address specific hazards related to their duties in industry, fire, EMT, CERTS, and other first responder areas. For example, a fire blanket may be contained in the case 20 that is used by fire first responders. The case 20 also may contain extra supply bags which contain a plurality of extra supplies in the event that more supplies are needed to address an emergency situation. The extra bags 22 may also contain non-disposable items that do not need to be disposed of after treating a victim, such as scissors, tweezers, or tape.

Figure 5:
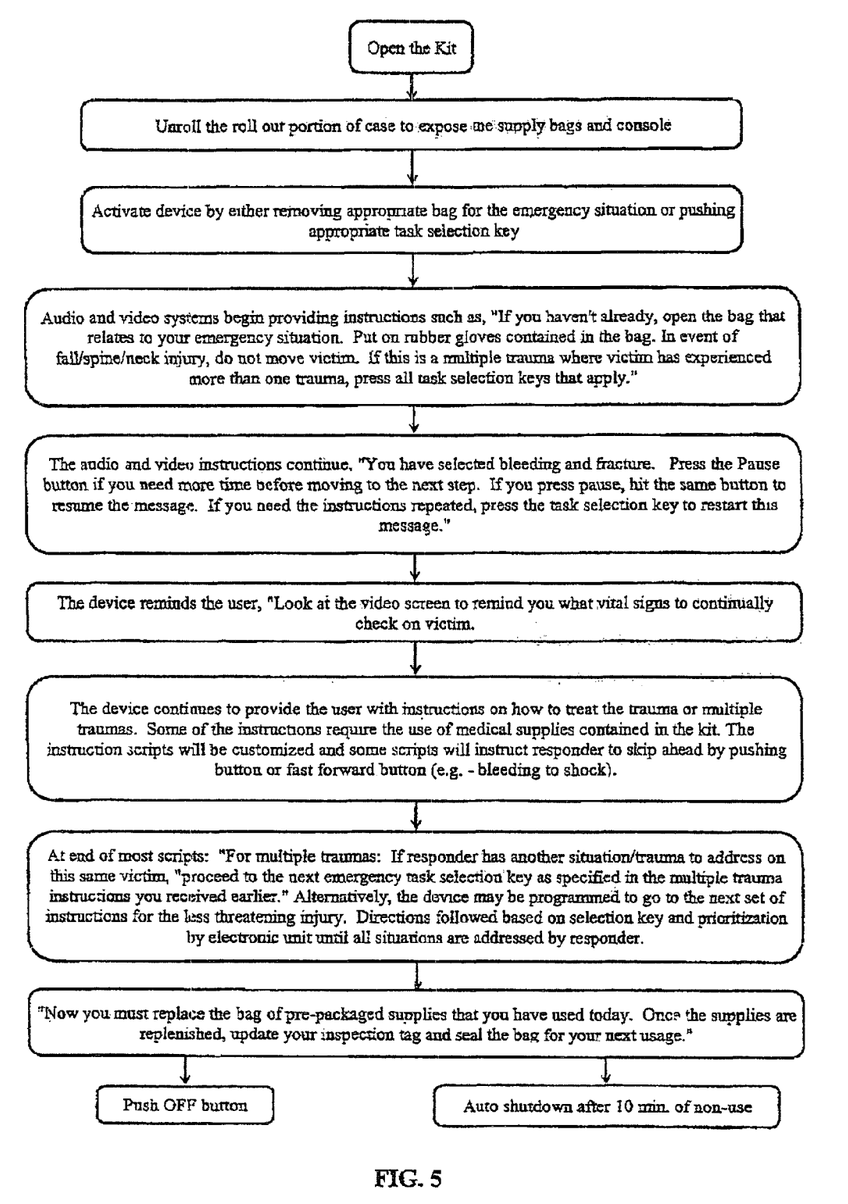
FIG. 5 is a flowchart showing exemplary general steps and possible instructional language used with the device.

FIG. 5 shows a flowchart for an exemplary use of the device. In use, the case 20 will be opened after a trauma has occurred. The user will either press one or more of the keys 32 or remove one or more of the break-away bags 22 to begin the programmed instructions. If more than one button 32 is pushed or more than one bag 22 is removed, the device will automatically prioritize the traumas and provide instructions in the proper order according to current medical standards, regardless of the order in which the keys 32 were pushed or bags 22 removed by the user. The user will open the selected bag 22 or bags and remove the medical supplies contained therein. The audio and/or video instructions will guide the user in properly treating the victim. The user can skip ahead, pause, or rewind portions of the instructions as the individual situation dictates. After an emergency response team has arrived and taken over care of the victim, the user can easily restock the supplies used by replacing the individual bags 22 used in treating the victim. The kit can be sealed with a plastic seal/inspection tag after restocking to show proper supplies are once again self-contained and to prevent confusion or harm caused by an unknown lack of emergency supplies contained in the kit.

Figure 7:
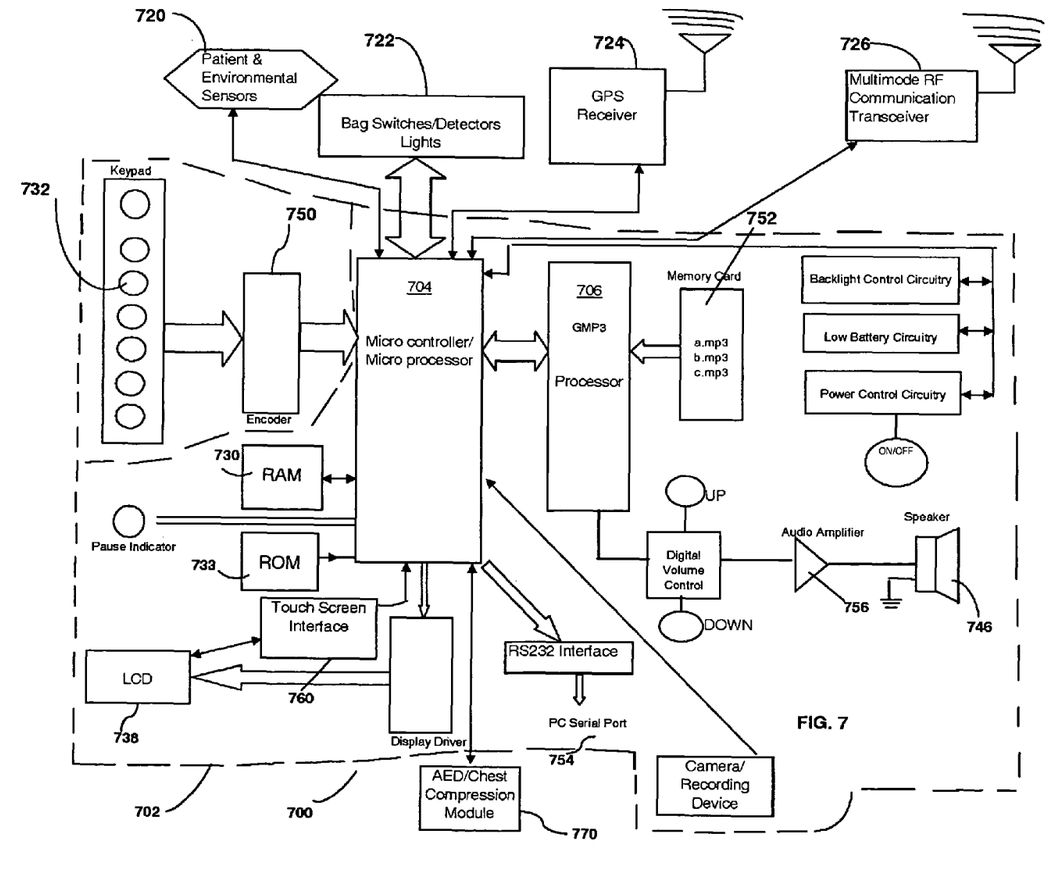
FIG. 7 is a block diagram of the circuitry of an alternate embodiment of the apparatus of the present invention. The area encircled by the intermittent line is a core electronic system such as used with a PDA or tablet PC.

Now referring to FIG. 7, there is shown a system generally designated 700 where the intermittent line 702 refers to a core portable multi-purpose digital computing system, such as a personal digital assistant (PDA), Pocket PC, or a laptop or tablet PC or other general purpose computing appliance, which is configured to run an operating system and various commercially available application programs. The system 700 could also be a dedicated system much like system 600 of FIG. 6. It is believed that a person skilled in the art could readily adapt the structures shown in FIG. 7 to either a dedicated machine or a PDA or multi-purpose machine.

If core portable multi-purpose digital computing system 702 is a commercially available PDA operating either the Pocket PC or Palm OS or other operating system, then the methods of the present invention could be executed in part by a program loaded onto the PDA and stored in ROM or RAM. The program could generate "soft keys" or "soft buttons" which are configurable with software and actuated via a touch screen. Alternately, physical buttons, dials, knobs, etc. can be manipulated for data entry. Otherwise the general overall functionality of interrogation and instructions provided by system 702 would be similar to the overall functionality of system 600.

System 700 further includes various other data input/output (I/O) components, such as patient sensors 720, which could include: a pulse oximeter, oxygen sensor; oxygen administration sensors and I/O; carbon dioxide monitor/gauge or respiratory sensor and data I/O; biological/chemical agent identification system; an ECG monitor; thermometer for patient and/or ambient temperature, camera, tape recorder, system recorder, or other sensors.

Bag switches or detectors 722 could perform the function of bag switches in FIG. 6 and could be in the form of RFID tags, photodetectors, or any other type of sensor or switch which would indicate to the processor 704 that bags or sets of first-aid supplies have either been removed, deployed or merely opened. This could be used to provide inventories of supplies as described above with respect to FIG. 6.

A GPS receiver 724 could be coupled to the microcontroller/microprocessor 704 and could provide information regarding the position of the system 700 when it is used where it has access to reception of GPS satellite signals. This information regarding position could then be transmitted via multi-mode RF communication transceiver 726, which could be a cell phone configured for operation on multiple frequencies, a satellite phone, two radios, wireless network components, or other wired or wireless communication means.

The system 700 is shown having a keypad 732 which could be a dedicated hardware component, keyboard or data input and output device, or it could be omitted if the microcontroller/microprocessor 704 is configured to provide and receive information to an LCD 738 with touch-screen data input capability via a touch-screen interface 760, which could be any suitable touch screen. The keypad 732 may be coupled through an encoder 750. The microcontroller 704 could be coupled with a Random Access Memory or (RAM) 730 and/or with a Read Only Memory or ROM 733.

Microcontroller/microprocessor 704 could be a single unit or be divided into separate processor 706 which could be dedicated to specific functions, such as audio signal processing and audio output generation and control. In one embodiment, a separate audio file memory card 752 could be deployed and used in conjunction with the processor 706, an audio amplifier 756 and a speaker 746.

Also shown in FIG. 7 is a PC serial port 754, which could be used to provide communication with external devices. Other types of ports or communication protocols could be substituted if suitable.

An AED charge delivery and chest compression module 770 could be provided to provide shocks for defibrillation, or it could perform chest compressions as part of CPR. Other systems, such as ventilator systems, could be employed as well.

Following is a description of the flow of the present invention. The flowchart for the other non-multiple injury aspects of the invention is even more simple and believed to be well within the level of skill in the art, and a person so skilled could readily create and adopt the necessary flowcharts and software code to carry out the present invention. Various protocols could be adopted or changed to determine how best to prioritize multiple injuries or multiple emergency situations. With the aid of the description herein, the Applicants believe that a person skilled in this art could make and use the presently claimed invention, without undue experimentation.

Software Sequence

Multiple Injury Button

Voice unit states and says on LCD screen:

"This button will help you assess and prioritize multiple injuries."

The priority that is followed is from American Heart Association (AHA) and American Red Cross (ARC) protocols that are typically referred to as the ABCs of prehospital care. There are many common reference materials for training laypersons with video or books/study guides from these associations. Typical training is done using these tools.

"Check scene safety and assess the area for any visual clues."

"Open the multiple injury supply pack or first aid kit and put on gloves and other personal protective items."

"Identify yourself. Obtain permission to proceed from the victim. If permission is denied—do not proceed. If the victim is unconscious or a minor, consent is implied."

The above is Good Samaritan language to protect the first responder from liability. Good Samaritan laws vary state to state. This language is optional in some states.

"If head/neck/spine injuries are suspected, do not move the victim."

"Check for consciousness and breathing. Press the CPR button if the victim is not breathing and/or does not have a pulse."

"Assign someone to call 9-1-1 immediately if it has not been called or seek advanced medical care onsite if available."

"Is this an infant over 1 year old? YES: Go to 1A. NO: Go to 1B.

1A. Check the pulse by putting 2 fingers on the inside of the upper arm between the elbow and shoulder. Does the infant have a pulse? YES: Go to 2A. NO: Go to CPR protocols within CPR button for an infant that are programmed. These are standard AHA and ARC protocols in a step-by-step flowchart. Concludes with 7B.

1B. Check for the pulse by putting two fingers on the side of the neck. Check for 10 seconds. Does the victim have a pulse? YES: Go to 2A. NO: Go to 2B.

2A. "Monitor the victim's airway, breathing and circulation. Press the CPR button if the victim loses pulse or stops breathing at any time."

"For head/neck/spine injuries, make sure the airway/head/neck is maintained. Do not address other injuries unless you can maintain head/neck."

"Check the victim's entire body for other signs of injury."

"Is the victim bleeding severely?" YES: Go to bleeding protocols that are programmed in the Bleeding button and are standard protocols per AHA/ARC. Concludes with 7B. NO: Go to 3A.

2B. Is the victim age 14 years or over (approximately the age of puberty or older)? YES: Go to CPR protocols within CPR button for an adult that are programmed. These are standard AHA and ARC protocols in step-by-step flowchart. Concludes with 7B. NO: Go to CPR protocols within CPR button for a child that are programmed. These are standard AHA and ARC protocols in a step-by-step flowchart. Concludes with 7B.

3A: "Has the victim been burned? YES: Go to the Burn protocols that are programmed in the Burn button and are standard protocols per AHA and ARC. Concludes with 7B. NO: Go to 4A.

4A: "Are there signs of broken bones or sprains? Signs include . . . (standard signs per AHA/ARC). YES: Go to Bone/Sprain protocols that are programmed in the Bone/Sprain button and are standard protocols per AHA and ARC. Concludes with 7B. NO: Go to 5A.

5A: "Press any other buttons as needed to address any other injuries or symptoms."

"Monitor the victim for signs of shock."

"Do you need information on the signs of shock?" YES: Go to 6A. NO: Go to 6B.

6A: "Signs of shock include (standard signs of shock per AHA/ARC . . . "

"Does the victim show signs of shock?" YES: Go to 7A. NO: Go to 7B.

6B: "Does the victim show signs of shock? YES: Go to 7A. NO: Go to 7B.

7A. Go to the Shock protocols that are programmed in the Bleeding/Shock button that are standard protocols per AHA/ARC. Concludes with 7B.

7B. "If the victim is stable, locate the emergency intake questionnaire or paper and pen."

"Gather whatever information you can about the emergency. There are specific questions to ask in the Responder's Handbook you can reference." These questions are standard ARC/AHA protocols used by first responders. In the future, the option may exist for them to pull the questions off a reference tool/menu on the hardware or software.

"Clean the areas of any body fluids/blood or other substances using proper precautions and a blood borne pathogen cleanup kit." We include a blood borne pathogen cleanup kit in most of our systems/kits. Some individuals or companies stock their own kits and so not all of our systems include this option.

"Wash your hands well and dispose of all affected items per proper biohazard protocols." These biohazard protocols are also standard ARC/AHA protocols.

"Press the arrow keys as needed for any emergency button to start over." END.

The proper SET system procedure would include inventory checks and restocking and rescaling of the system before putting back on the wall. It is not a requirement of the system to be tagged with a pull tight lock, but it is preferred so that the next user knows it is fully stocked and ready for use.

Having thus described the invention in connection with the preferred embodiments thereof, it will be evident to those skilled in the art that various revisions can be made to the preferred embodiments described herein without departing from the spirit and scope of the invention. It is my intention, however, that all such revisions and modifications that are evident to those skilled in the art will be included within the scope of the following claims.

What is claimed is as follows:

1. A method of providing an emergency responder with prioritized audible instruction assistance comprising the steps of:
   providing a portable, battery-powered, electronic device, configured to provide one of a plurality of audible instruction sets for predetermined emergency situations when one of a plurality of switches is activated wherein each of the plurality of switches is associated with one of a plurality of traumas and corresponds to one of a plurality of sets of supplies adapted to treat the associated trauma; and
   receiving a plurality of signals representative of the fact that the plurality of switches have been activated; and in response thereto, prioritizing provisioning of the plurality of audible instruction sets based upon a predetermined prioritization algorithm which determines relative medical urgency levels for each of the plurality of switches activated.

2. The method of claim 1 further comprising the steps of: in response to receiving an individual or a plurality of signals, determining if additional information is necessary to prioritize a plurality of emergency situation instruction sets and issuing a request for additional information if more information is needed to make a proper prioritization.

3. The method of claim 2 wherein the plurality of switches are a plurality of soft switches which are part of a touch-screen display.

4. The method of claim 1 further comprising the steps of providing a GPS receiver and determining a geographic location of the electronic device and transmitting information representative of the geographic location.

5. The method of claim 1 further comprising the steps of: monitoring a plurality of sets of supplies to determine if any have been deployed; and providing a report that one of the plurality of sets of supplies has been deployed.

6. The method of claim 5 wherein the report is an inventory of the plurality of sets of supplies.

7. The method of claim 6 wherein the report is transmitted electronically via a radio communication link.

8. The method of claim 5 wherein the step of monitoring comprises detecting a change of status of a bag of supplies from a predetermined location in a plurality of bags of differing supplies.

9. The method of claim 8 wherein the change of status is a change of location.

10. The method of claim 8 wherein the change of status is caused by opening a bag.

11. The method of claim 1 wherein the electronic device is a handheld multi-purpose personal digital assistant with an operating system which is configured to execute a plurality of personal information management-related programs and which has a touch screen which is configured to have soft keys and wherein the plurality of personal information management programs comprises a calendar program, a task program, and an address book program.

12. An apparatus for aiding emergency response providers comprising:
    a portable battery-powered electronic device, configured to execute software resident on the electronic device;
    the software being configured to receive a plurality of indications of simultaneous medical conditions requiring first aid based upon the activation of a plurality of switches wherein each of the plurality of switches is associated with one of a plurality of traumas and corresponds to one of a plurality of sets of supplies adapted to treat the associated trauma;
    the software further configured to prioritize the plurality of indications in accordance with a predetermined medical criteria, and first provide audible instructions to aid in delivery of first aid for a first one of the plurality of indications which corresponds to a first-highest priority situation and thereafter provide a delayed delivery of instructions for first aid for a second one of the plurality of indications which corresponds to a second-highest priority situation.

13. An apparatus of claim 12 further comprising: means for monitoring a deployment of a set of supplies and for generating a report indicating that a set of supplies has been deployed.

14. An apparatus of claim 13 further comprising means for communicating the report.

15. An apparatus of claim 13 wherein a display device communicates the report.

16. An apparatus of claim 13 wherein a communication transceiver communicates the report.

17. An apparatus of claim 12 wherein the electronic device comprises a handheld, portable, battery-operated personal digital assistant.

18. An apparatus of claim 12 further comprising an automatic external defibrillator.

19. An apparatus of claim 18 further comprising patient sensors.

20. A method of aiding first-aid providers comprising the steps of:
    providing a handheld, battery-operated personal digital assistant which is configured to execute a prioritizing emergency response/first-aid assistance application program;
    wherein the prioritizing emergency response/first-aid assistance application program is configured to receive a plurality of inputs from a user with respect to one patient, where each of the plurality of inputs corresponds to an indication that the patient has simultaneous medical conditions which might require emergency response or first aid and wherein the inputs are provided by a user activating a plurality of switches wherein each of the plurality of switches is associated with one of a plurality of traumas and corresponds to one of a plurality of sets of supplies adapted to treat the associated trauma;

determining whether a request for additional information is necessary before a prioritization decision can be made;

prioritizing the plurality of inputs using the prioritizing emergency response/first-aid assistance application software program and generating an instruction set which provides the user with emergency response instructions for a first of the plurality of inputs which corresponds to a highest priority medical condition or emergency situation; and delaying providing information with respect to a second-highest priority medical condition until first-aid instruction is provided with respect to the highest priority emergency situation.

* * * * *